United States Patent
Vissapragada Venkata Satya et al.

(10) Patent No.: US 11,154,256 B2
(45) Date of Patent: Oct. 26, 2021

(54) DETECTING MOUTH-BREATHING IN EARLY PHASE EXPIRATION

(71) Applicant: KONINKLIJKE PHILIPS N.V., Eindhoven (NL)

(72) Inventors: Surya Subrahmanya Sreeram Vissapragada Venkata Satya, Pittsburgh, PA (US); Leonardo Alberto Baloa Welzien, Lake Forest, CA (US); Manuel Laura Lapoint, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 921 days.

(21) Appl. No.: 14/351,203

(22) PCT Filed: Oct. 11, 2012

(86) PCT No.: PCT/IB2012/055498
§ 371 (c)(1),
(2) Date: Apr. 11, 2014

(87) PCT Pub. No.: WO2013/057635
PCT Pub. Date: Apr. 25, 2013

(65) Prior Publication Data
US 2014/0276168 A1    Sep. 18, 2014

Related U.S. Application Data

(60) Provisional application No. 61/548,873, filed on Oct. 19, 2011.

(51) Int. Cl.
| | |
|---|---|
| *A61M 16/00* | (2006.01) |
| *A61B 5/00* | (2006.01) |
| *A61B 5/087* | (2006.01) |
| *A61M 16/16* | (2006.01) |
| *A61B 5/08* | (2006.01) |
| *A61M 16/10* | (2006.01) |

(52) U.S. Cl.
CPC ............ *A61B 5/7282* (2013.01); *A61B 5/087* (2013.01); *A61B 5/0826* (2013.01);
(Continued)

(58) Field of Classification Search
CPC ..... A61M 16/00–0012; A61M 16/0051–0084; A61M 16/0096;
(Continued)

(56) References Cited

U.S. PATENT DOCUMENTS

| | | | |
|---|---|---|---|
| 5,503,146 A | | 4/1996 | Froehlich et al. |
| 5,551,419 A | * | 9/1996 | Froehlich .......... A61M 16/0069 128/204.23 |

(Continued)

FOREIGN PATENT DOCUMENTS

| | | |
|---|---|---|
| EP | 0722747 A2 | 7/1996 |
| EP | 0788805 A2 | 8/1997 |

*Primary Examiner* — Jan Christopher L Merene
*Assistant Examiner* — Ned T Heffner (57) ABSTRACT

Mouth-breathing can be detected in early phase expiration during respiratory treatments involving a pressure support device. In accordance with some embodiments, an output signal is received from a sensor that conveys information relating to one or more parameters of the pressurized flow of breathable gas as it is delivered to an air-way of a subject. Transitions are estimated between inspiratory phases and expiratory phases of respiration by the subject based on the one or more determined parameters. A local extreme is identified in a level of a first parameter during a given expiratory phase of respiration by the subject. The level of the first parameter is analyzed as a function of time within a sampling window to determine whether the subject is breathing by mouth during the given expiratory phase. The sampling window begins at or proximate to the identified local extreme in the level of the first parameter.

14 Claims, 4 Drawing Sheets

(52) U.S. Cl.
CPC .......... *A61B 5/4836* (2013.01); *A61B 5/7278* (2013.01); *A61M 16/0003* (2014.02); *A61M 16/0069* (2014.02); *A61M 16/024* (2017.08); *A61M 16/161* (2014.02); *A61M 2016/003* (2013.01); *A61M 2016/0027* (2013.01); *A61M 2016/0039* (2013.01); *A61M 2016/102* (2013.01); *A61M 2205/332* (2013.01); *A61M 2205/3368* (2013.01); *A61M 2205/3375* (2013.01); *A61M 2230/43* (2013.01)

(58) Field of Classification Search
CPC .......... A61M 16/04–0402; A61M 16/06–0661; A61M 2016/0015–0042; A61M 2230/00; A61M 2230/005; A61M 2230/202–205; A61M 2230/40–46; A61M 16/22; A61B 5/082–097
See application file for complete search history.

(56) References Cited

U.S. PATENT DOCUMENTS

| | | |
|---|---|---|
| 6,105,575 A | 8/2000 | Estes et al. |
| 2005/0076906 A1 | 4/2005 | Johnson |
| 2006/0037614 A1 | 2/2006 | Madaus et al. |
| 2008/0119755 A1* | 5/2008 | Schatzl ................ A61B 5/4818 600/538 |
| 2010/0186741 A1 | 7/2010 | Aylsworth et al. |

* cited by examiner

DETECTING MOUTH-BREATHING IN EARLY PHASE EXPIRATION

This disclosure relates to detecting mouth-breathing in early phase expiration during respiratory treatments involving a pressure support device.

It is known to treat a medical disorder or to diagnose, treat, or monitor the condition of a subject using medical equipment. For example, subjects suffering from a pulmonary or respiratory disorder, such as obstructive sleep apnea (OSA), are often treated with a pressure support device. One example of such a pressure support device is a continuous positive airway pressure (CPAP) device. A CPAP device delivers a flow of fluid to the airway of the subject throughout the subject's breathing cycle in order to "splint" the airway, thereby preventing its collapse during sleep.

Another example of a pressure support device provides a bi-level positive pressure therapy, in which the pressure of fluid delivered to the subject's airway varies or is synchronized with the subject's breathing cycle to maximize the medical effect and/or comfort to the subject. This type of device may be known as a bi-level positive airway pressure (BiPAP) device. With some BiPAP devices, a lower pressure is delivered to the subject during the subject's expiratory phase than during the inspiratory phase. It is also known to provide an auto-titration positive pressure therapy in which the pressure provided to the subject changes based on detected conditions of the subject. Such detected conditions may include whether the subject is snoring or experiencing an apnea, hypopnea, or upper airway resistance.

Once a subject is diagnosed with a breathing disorder, he or she is typically prescribed a pressure support therapy, i.e., a mode of pressure support (e.g., continuous, bi-level, or auto-titration), and given a prescribed pressure support level. The pressure support therapy (mode of pressure support and pressure settings) is typically prescribed by a physician after the subject undergoes a sleep study at a sleep lab.

In treating a subject using any of the above-described pressure support systems, each of which represents a mode of providing pressure support, it is often desirable to monitor various parameters associated with the use of such systems. Typically, leak on a pressure support device is continuously or periodically estimated based on the total flow of fluid provided by the pressure support device between the start and the end of a breath. The estimated leak is then subtracted from the total flow of fluid provided by the pressure support device to estimate the flow of fluid delivered to the subject. By way of non-limiting example, parameters such as tidal volumes, peak flows, inspiration/expiration (FE) states, and/or other parameters are derived from the estimate of the flow of fluid delivered to the subject. Therefore, accurate estimation of various parameters often depends on accurate estimation of the leak.

A subject with upper airway respiratory abnormalities often breathes using his/her mouth. When the subject uses a pressure support device, he/she inspires through the nose because there is a higher pressure at the nose. However, the subject sometimes expires through the mouth because there is lesser pressure at the mouth. This phenomenon of mouth-breathing during expiration can be observed, for example, on subjects suffering from OSA and/or other pulmonary or respiratory disorders. Mouth-breathing dampens or otherwise affects the estimation of the flow of fluid delivered to the subject as some flow is lost through the mouth.

Accordingly, it is an object of the present invention to detect mouth-breathing in early phase expiration during respiratory treatments involving a pressure support device to overcome the shortcomings of conventional approaches to leak estimation. This object is achieved according to one aspect of the present invention by providing a system configured for detecting mouth-breathing in early phase expiration during respiratory treatments involving a pressure support device. The system includes a pressure generator, a sensor, and one or more processors. The pressure generator is configured to generate a pressurized flow of breathable gas for delivery to the airway of a subject. The sensor is configured to provide an output signal conveying information relating to one or more parameters of the pressurized flow of breathable gas as it is delivered to the airway of the subject. The one or more processors are configured to execute computer program modules. The computer program modules comprise a parameter module, a breath delineation module, a parameter extrema module, and a mouth-breathing detection module. The parameter module is configured to determine one or more parameters of the pressurized flow of breathable gas as it is delivered to the airway of the subject based on the output signal. The one or more parameters comprise a first parameter. The breath delineation module is configured to estimate transitions between inspiratory phases and expiratory phases of respiration by the subject based on the one or more parameters determined by the parameter module. The parameter extrema module is configured to identify a local extreme in a level of the first parameter during a given expiratory phase of respiration by the subject. The mouth-breathing detection module is configured to determine whether the subject is breathing by mouth during the given expiratory phase by analyzing the level of the first parameter as a function of time within a sampling window. The sampling window begins at or proximate to the identified local extreme in the level of the first parameter.

Another aspect of the invention relates to a method for detecting mouth-breathing in early phase expiration during respiratory treatments involving a pressure support device. The method includes receiving an output signal from a sensor. The output signal conveys information relating to one or more parameters of the pressurized flow of breathable gas as it is delivered to an airway of a subject. The method includes determining one or more parameters of the pressurized flow of breathable gas as it is delivered to the airway of the subject based on the output signal. The one or more parameters comprise a first parameter. The method includes estimating transitions between inspiratory phases and expiratory phases of respiration by the subject based on the one or more determined parameters. The method includes identifying a local extreme in a level of the first parameter during a given expiratory phase of respiration by the subject. The method includes analyzing the level of the first parameter as a function of time within a sampling window to determine whether the subject is breathing by mouth during the given expiratory phase. The sampling window begins at or proximate to the identified local extreme in the level of the first parameter.

Yet another aspect of the invention relates to a system configured for detecting mouth-breathing in early phase expiration during respiratory treatments involving a pressure support device. The system includes pressure generation means, sensor means, parameter determination means, breath delineation means, minimum flow identification means, and mouth-breathing detection means. The pressure generation means is configured to generate a pressurized flow of breathable gas for delivery to the airway of a subject. The sensor means is configured to provide an output signal conveying information relating to one or more parameters of the pressurized flow of breathable gas as it is delivered to the airway of the subject. The parameter determination means is configured to determine one or more parameters of the pressurized flow of breathable gas as it is delivered to the airway of the subject based on the output signal. The one or more parameters comprise a first parameter. The breath delineation means is configured to estimate transitions between inspiratory phases and expiratory phases of respiration by the subject based on the one or more determined parameters. The minimum flow identification means is configured to identify a local extreme in a level of the first parameter during a given expiratory phase of respiration by the subject. The mouth-breathing detection means is configured to determine whether the subject is breathing by mouth during the given expiratory phase by analyzing the level of the first parameter as a function of time within a sampling window. The sampling window beginning at or proximate to the identified local extreme in the level of the first parameter.

These and other objects, features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the technology, the structural components illustrated herein are drawn to scale. It is to be expressly understood, however, that the drawings are for the purpose of illustration and description only and are not a limitation of the technology. In addition, it should be appreciated that structural features shown or described in any one embodiment herein can be used in other embodiments as well. It is to be expressly understood, however, that the drawings are for the purpose of illustration and description only and are not intended as a definition of the limits of the technology.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Exemplary embodiments solve or greatly alleviate one or more deficiencies of conventional approaches to leak estimation in pressure support devices when mouth-breathing occurs. For example, detection of mouth-breathing can be used to provide an indication of abnormalities in a fluid flow pattern during a leak estimation procedure. Mouth-breathing detection can improve I/E triggering of a pressure support device. Mouth-breathing can be reported as a subject event to a healthcare provider. Nasal resistance, which can lead to low compliance with a particular breathing interface, may be indicated by mouth breathing.

Figure 1:
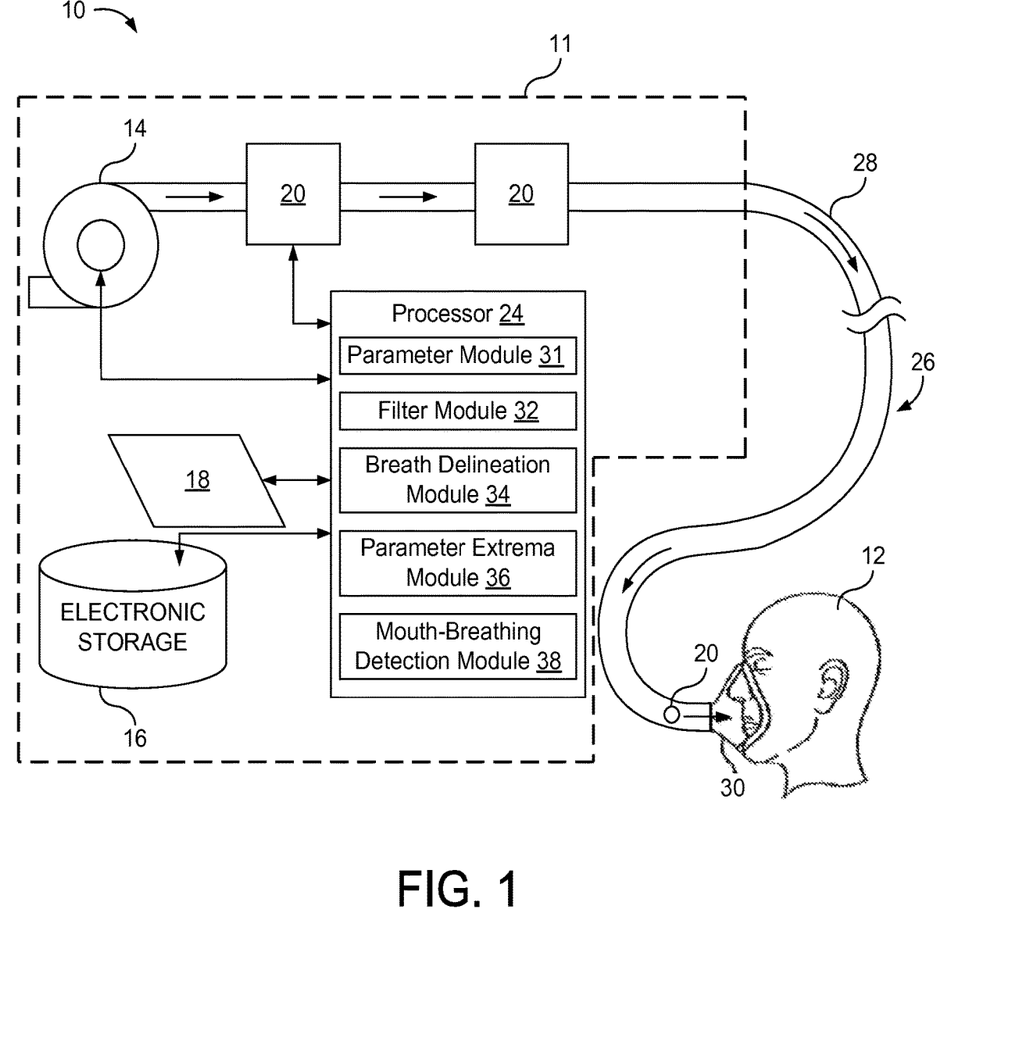
FIG. 1 illustrates a system configured for detecting mouth-breathing in early phase expiration during respiratory treatments involving a pressure support device, in accordance with one or more embodiments.

FIG. 1 illustrates a system 10 configured for detecting mouth-breathing in early phase expiration during respiratory treatments involving a pressure support device 11, in accordance with one or more embodiments. During the respiratory treatments, a pressurized flow of breathable gas is delivered to the airway of a subject 12 in accordance with a therapy regimen. The therapy regimen may be designed to treat a respiratory condition, such as Obesity Hypoventilation Syndrome, Obstructive Sleep Apnea, and/or other pulmonary or respiratory disorders. In one embodiment, system 10 includes one or more of a pressure generator 14, electronic storage 16, a user interface 18, one or more sensors 20, a processor 24, and/or other components.

In one embodiment, pressure generator 14 is configured to generate a pressurized flow of breathable gas for delivery to the airway of subject 12. The pressure generator 14 may control one or more parameters of the pressurized flow of breathable gas (e.g., flow, pressure, volume, humidity, temperature, gas composition, etc.) for therapeutic purposes, or for other purposes. The one or more parameters may be controlled in accordance with a therapy regimen (e.g., as discussed further below). The therapy regimen may be configured to sustain and/or otherwise improve the quality of life in subject 12. By way of non-limiting example, pressure generator 14 may be configured to control the pressure of the pressurized flow of breathable gas in order to treat respiratory insufficiency or obstructed airway syndrome. The pressure generator 14 may include a positive pressure generator configured to provide a positive airway pressure therapy to subject 12. Such a device is described, for example, in U.S. Pat. No. 6,105,575, hereby incorporated by reference in its entirety.

The pressurized flow of breathable gas is delivered to the airway of subject 12 via a subject interface 26. Subject interface 26 is configured to communicate the pressurized flow of breathable gas generated by pressure generator 14 to the airway of subject 12. As such, subject interface 26 includes a conduit 28 and an interface appliance 30. Conduit 28 conveys the pressurized flow of breathable gas to interface appliance 30, and interface appliance 30 delivers the pressurized flow of breathable gas to the airway of subject 12. Some examples of interface appliance 30 may include, for example, an endotracheal tube, a nasal cannula, a nasal mask, a nasal/oral mask, a full face mask, a total face mask, or other interface appliances configured to communicate a flow of gas with an airway of a subject. The present invention is not limited to these examples, and contemplates delivery of the pressurized flow of breathable gas to subject 12 using any subject interface.

Although FIG. 1 illustrates the configuration of system 10 with subject interface 26 as being a single-limb, passive system, this is not intended to be limiting. It will be appreciated that the scope of this disclosure includes embodiments in which the subject interface 26 is formed as a two-limbed system including a second conduit configured to receive exhalation from interface appliance 30. The second conduit may exhaust such fluid to atmosphere, may convey such fluid to a filter, and/or convey such fluid to other components including a component within system 10.

In one embodiment, electronic storage 16 comprises electronic storage media that electronically stores information. The electronic storage media of electronic storage 16 may include one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 16 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 16 may store software algorithms, information determined by processor 24, information received via user interface 18, and/or other information that enables system 10 to function properly. Electronic storage 16 may be (in whole or in part) a separate component within system 10, or electronic storage 16 may be provided (in whole or in part) integrally with one or more other components of system 10 (e.g., pressure generator 14, user interface 18, processor 24, and/or other components of system 10).

User interface 18 is configured to provide an interface between system 10 and one or more users (e.g., subject 12, a caregiver, a researcher, a therapy decision-maker, and/or other users) through which the users may provide information to and receive information from system 10. This enables data, cues, results, and/or instructions and any other communicable items, collectively referred to as "information," to be communicated between the users and one or more of pressure generator 14, electronic storage 16, processor 24, and/or other components of system 10. Examples of interface devices suitable for inclusion in user interface 18 include a keypad, buttons, switches, a keyboard, knobs, levers, a display screen, a touch screen, speakers, a microphone, an indicator light, an audible alarm, a printer, a tactile feedback device, and/or other interface devices. In one embodiment, user interface 18 includes a plurality of separate interfaces. In one embodiment, user interface 18 includes at least one interface that is provided integrally with pressure generator 14. User interface 18 may be configured to receive input from subject 12 to modify tunable parameters of system 10. For example, user interface 18 may be configured to receive input from subject 12 to modify or select sensitivity or response time of the respiratory state detection (e.g., the threshold level for breathing state transition detection may be adjusted for either an increase or a decrease in sensitivity with a graduated knob or a digital interface displaying a number from 1 to 10).

It is to be understood that other communication techniques, either hard-wired or wireless, are also contemplated by the present invention as user interface 18. For example, the present invention contemplates that user interface 18 may be integrated with a removable storage interface provided by electronic storage 16. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 18 include, but are not limited to, an RS-232 port, RF link, an IR link, modem (telephone, cable or other). In short, any technique for communicating information with system 10 is contemplated by the present invention as user interface 18.

The sensors 20 are configured to generate one or more output signals conveying information related to respiratory effort of subject 12 and/or a flow of fluid during breathing of subject 12. The fluid may include inspired breathable gas, expired breathable gas, and/or other breathable fluid. In one embodiment, sensors 20 generate output signals conveying information related to one or more parameters of the pressurized flow of breathable gas as it is delivered to the airway of the subject. The one or more parameters may include, for example, one or more of a flow, a volume, a pressure, a composition (e.g., concentration(s) of one or more constituents), humidity, temperature, acceleration, velocity, acoustics, changes in a parameter indicative of respiration, and/or other fluid parameters. In one embodiment sensors 20 are a flow sensor and a pressure sensor. The sensors 20 may include one or more sensors that measure such parameters directly (e.g., through fluid communication with the pressurized flow of breathable gas at pressure generator 14 or in subject interface 26). The sensors 20 may include one or more sensors that generate output signals related to one or more fluid parameters of the pressurized flow of breathable gas indirectly. For example, one or more of sensors 20 may generate an output based on an operating parameter of pressure generator 14 (e.g., a valve driver or motor current, voltage, rotational velocity, and/or other operating parameters), and/or other sensors.

Other output signals conveying information related to respiratory effort are contemplated. For example, sensors 20 may include a sensor that mechanically detects respiratory muscle effort (e.g., worn on a band around the chest of subject 12), an optical sensor that captures images of subject 12 and/or measures the position and/or motion (e.g., velocity or acceleration) of subject 12.

Although sensors 20 are illustrated as two separate sensors disposed adjacent to pressure generator 14 and one separate sensor disposed adjacent to interface appliance 30, this is not intended to be limiting. The sensors 20 may include one or more sensors disposed in single location or a plurality of locations, such as for example, within pressure generator 14, within (or in communication with) conduit 28, within (or in communication with) interface appliance 30, and/or other locations.

In some implementations, one or more of sensors 20 may be placed outside of system 10 and nearer to subject 12. In such implementations, the output signals generated by the externally located sensors 20 can be relayed to processor 24 by wired and/or wireless configuration. An independent user interface may be included with the externally located sensors 20 that receives the output signals generated by sensors 20, processes the output signals implementing some or all of the techniques described herein, and/or displaying at least some of the determined information.

Processor 24 is configured to provide information processing capabilities in system 10. As such, processor 24 may include one or more of a digital processor, an analog processor, a digital circuit designed to process information, an analog circuit designed to process information, a state machine, and/or other mechanisms for electronically processing information. Although processor 24 is shown in FIG. 1 as a single entity, this is for illustrative purposes only. In some implementations, processor 24 may include a plurality of processing units. These processing units may be physically located within the same device (e.g., pressure generator 14), or processor 24 may represent processing functionality of a plurality of devices operating in coordination.

As is shown in FIG. 1, processor 24 may be configured to execute one or more computer program modules. The one or more computer program modules may include one or more of a parameter module 31, a filter module 32, a breath delineation module 34, a parameter extrema module 36, a mouth-breathing detection module 38, and/or other modules. Processor 24 may be configured to execute modules 31, 32, 34, 36, and/or 38 by software; hardware; firmware; some combination of software, hardware, and/or firmware; and/or other mechanisms for configuring processing capabilities on processor 24.

It should be appreciated that although modules 31, 32, 34, 36, and 38 are illustrated in FIG. 1 as being co-located within a single processing unit, in implementations in which processor 24 includes multiple processing units, one or more of modules 31, 32, 34, 36, and/or 38 may be located remotely from the other modules. The description of the functionality provided by the different modules 31, 32, 34, 36, and/or 38 described below is for illustrative purposes, and is not intended to be limiting, as any of modules 31, 32, 34, 36, and/or 38 may provide more or less functionality than is described. For example, one or more of modules 31, 32, 34, 36, and/or 38 may be eliminated, and some or all of its functionality may be provided by other ones of modules 31, 32, 34, 36, and/or 38. As another example, processor 24 may be configured to execute one or more additional modules that may perform some or all of the functionality attributed below to one of modules 31, 32, 34, 36, and/or 38.

The parameter module 31 is configured to determine one or more parameters of the pressurized flow of breathable gas as it is delivered to the airway of the subject based on the output signal of sensor 20. As mentioned above, the one or more parameters may include, for example, one or more of a flow, a volume, a pressure, a composition (e.g., concentration(s) of one or more constituents), humidity, temperature, acceleration, velocity, acoustics, changes in a parameter indicative of respiration, and/or other fluid parameters.

Figure 2A:
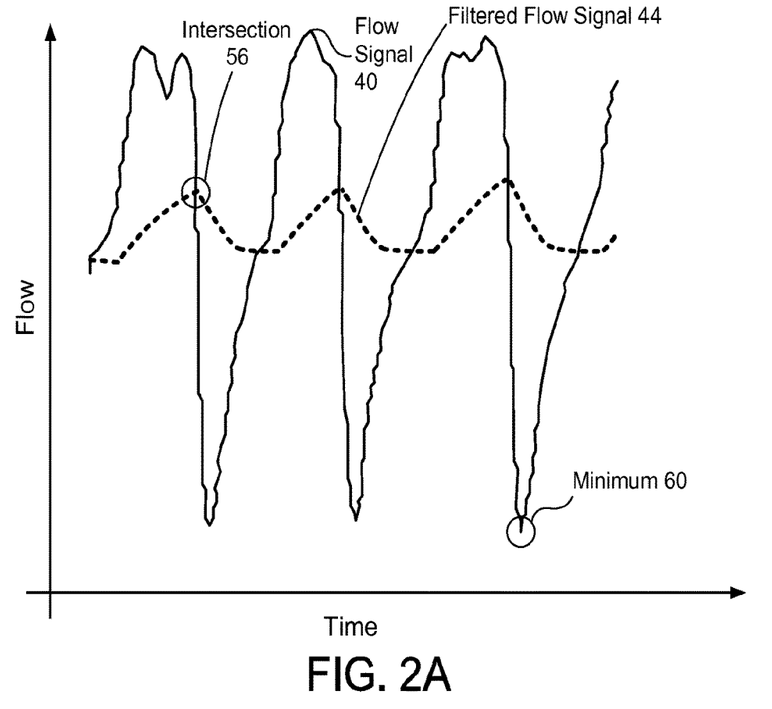
FIGS. 2A and 2B illustrate exemplary plots of various flow signals during breathing.
Figure 2B:
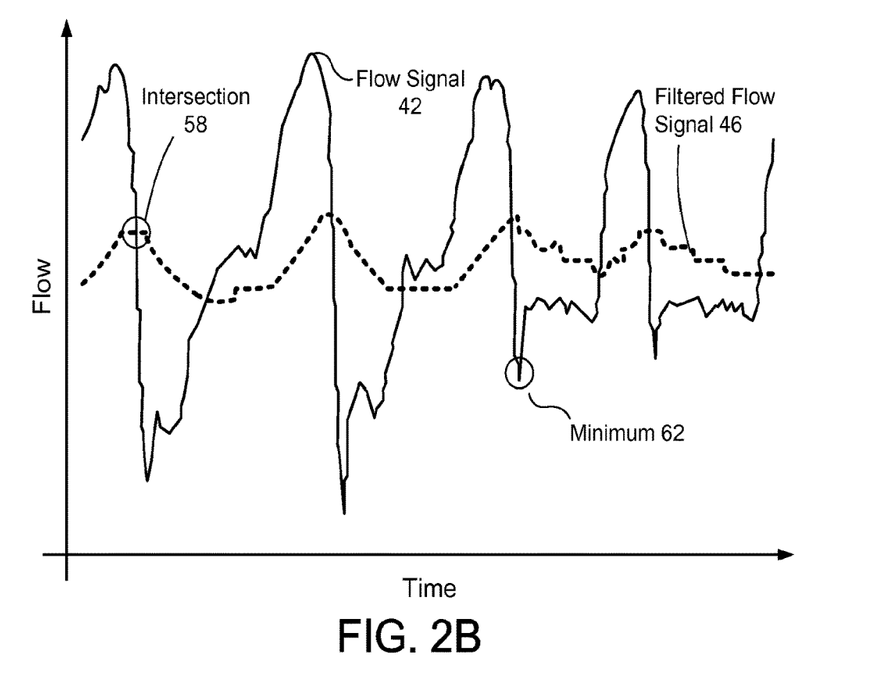

FIGS. 2A and 2B illustrate exemplary plots of various flow signals during breathing. More specifically, FIG. 2A illustrates a plot of a flow signal 40 as a function of time from normal breaths, while FIG. 2B shows a plot of a flow signal 42 as a function of time from breaths where mouth-breathings is occurring. In some embodiments, the flow signals 40 and 42 determined as parameters based on output signals from sensors 20. Here, the flow signals 40 and 42 represent the flow of breathable gas passing through interface appliance 30, according to some embodiments.

When mouth-breathing occurs, as opposed to nose-breathing, there is a decrease in the flow of fluid through the nose. Mouth-breathing during expiration is characterized by a decrease in flow rate in flow signal 42 during an expiratory phase. That is, mouth-breathing dampens flow signal 42 during expiration. For a normal breath during expiration, flow signal 40 decreases rapidly to a minimum flow, gradually increases back to a base-line flow, and then increases rapidly again at the start of the next inspiration. However, for mouth-breathing breaths, flow signal 42 looses its positive gradient and flattens out when the mouth is recruited to exhale. Mouth-breathing distorts flow signal 42 (as compared to flow signal 40) more during early expiration than during the end an expiratory phase. This is because the flow rate of an exhalation is higher at the start of expiration than towards its end.

Referring again to FIG. 1, filter module 32 is configured to provide a filtered signal by suppressing high-frequency components of a flow signal (e.g., flow signal 40 and/or flow signal 42) and/or other output signals from sensor 20 or derivations therefrom. In FIG. 2A, filtered flow signal 44 represents a result of filtering flow signal 40. Similarly, in FIG. 2B, filtered flow signal 46 represents a result of filtering flow signal 42. By way of non-limiting example, the filter module 32 may process a flow signal (or other output signal) by smoothing, filtering (e.g., high-pass, low-pass, band-pass, etc.), and/or other processing techniques. According to some embodiments, a flow signal (e.g., flow signal 40 and/or flow signal 42) is filtered to suppress high-frequency components and only pass low-frequency components. High-frequency components may include components of a signal higher than approximately 0.2 Hz. Low-frequency components may include components of a signal lower than approximately 0.1 Hz.

The breath delineation module 34 is configured to estimate transitions between inspiratory phases and expiratory phases of respiration by the subject. In some embodiments, such an estimation is based on one or more parameters determined by gas parameter module 31 (e.g., flow signal 40 and/or flow signal 42), other output signals from sensor 20, and/or other information associated with breathing by the subject. Transitions between inspiratory phases and expiratory phases can be estimated based on a filtered flow signal (e.g., filtered flow signal 44 and/or filtered flow signal 46) and/or other filtered output signals from sensor 20.

Figure 3:
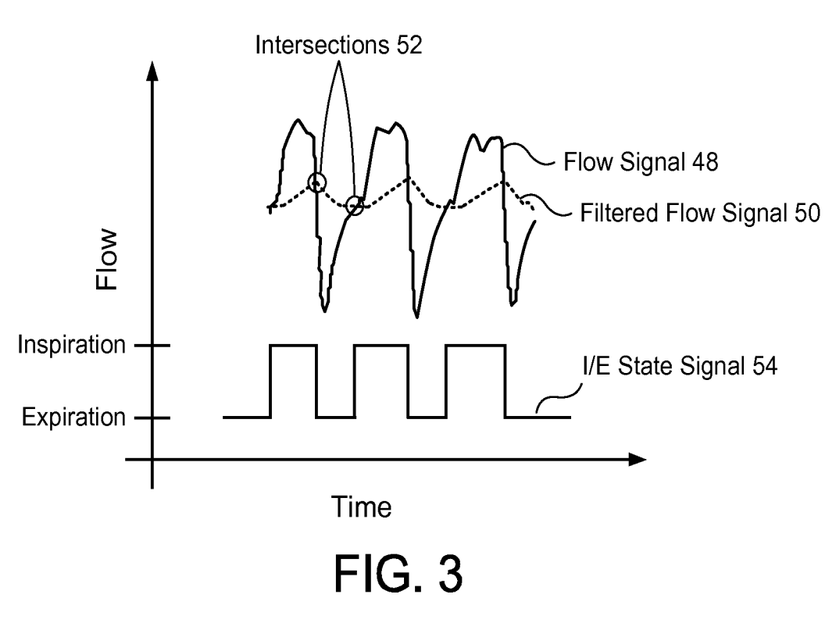
FIG. 3 illustrates an exemplary approach to estimating transitions between inspiratory phases and expiratory phases of respiration by the subject, according to one or more embodiments.

FIG. 3 illustrates an exemplary approach to estimating transitions between inspiratory phases and expiratory phases of respiration by the subject, according to one or more embodiments. In FIG. 3, a flow signal 48 is plotted together with a filtered flow signal 50. In some embodiments, estimating transitions between inspiratory phases and expiratory phases includes identifying points where a filtered flow signal (e.g., filtered flow signal 50) intersects a flow signal (e.g., flow signal 48). Examples of such intersections are shown in FIG. 3 as intersections 52. Corresponding estimated respiratory states are indicated by I/E state signal 54, where a high value is associated with an inspiratory phase and a low value is associated with an expiratory phase.

Turning back to FIG. 1, parameter extrema module 36 is configured to identify a local extreme (e.g., a minimum or maximum) in a level of the first gas parameter during a given expiratory phase of respiration by subject 12. Generally speaking, there is typically a sharp gradient in slope of a flow signal, for a given breath, from the point of maximum flow during inspiration to the point of minimum flow during expiration. FIGS. 2A and 2B show how a flow curve decreases from an inspiration-to-expiration transition (see, e.g., intersection 56 and/or intersection 58) to the minimum flow for both normal and mouth-breathing breaths. Minimum 60 and minimum 62 represent examples of such minimum flows during expiration.

The mouth-breathing detection module 38 is configured to determine whether the subject is breathing by mouth during the given expiratory phase by analyzing the level of the first gas parameter as a function of time within a sampling window. The sampling window begins at or proximate to the identified local extreme. As mentioned above, the local extreme in the level of the first parameter may be a local minimum. In exemplary embodiments, a duration of the sampling window is less than a duration of the given breath. For example, the sampling window can have a duration of one second or some other duration. According to some embodiments, analyzing the output signal within the sampling window includes determining whether the output signal within the sampling window increases initially and then becomes flat or decreasing, and wherein a positive determination indicates an occurrence of mouth-breathing by the subject.

For a normal breath, a flow signal is expected to be an increasing function before it flattens out towards the end of expiration. However, when there is mouth-breathing during early expiration, the flow is an increasing function only briefly before it flattens out because some of the flow is going through the mouth (see, e.g., FIGS. 2A and 2B). In some embodiments, such flattening may be identified in order to indicate an occurrence of mouth-breathing. One may let $Q_i$ be the $i^{th}$ sample of the total flow signal from the point of minimum flow of each breath where i≥0. Accordingly, $\overline{Q}_j$ is the average flow of the n samples of $Q_i$, such that:

$$\overline{Q}_j = \frac{1}{n} \sum_{jn}^{(j+1)n-1} Q_i, \quad \text{(EQN. 1)}$$

where j=(0, 1, 2, . . . ). For a normal breath, the gradient of $\overline{Q}_j$ should be greater than zero initially from the point of minimum flow. Accordingly, a mouth-breathing breath can be identified where the gradient of $\overline{Q}_j$ is less than or equal to zero from the point of minimum flow. That is, $(Q_j-Q_{j-1})\leq0$ for j>0.

Taking the average of n samples is equivalent to downsampling the flow signal. As such, n should be chosen so the time interval to determine the gradient of the flow signal is large enough to negate any inherent variance from sensor 20 and small enough to capture any discrepancy from the normal breathing flow behavior.

Figure 4:
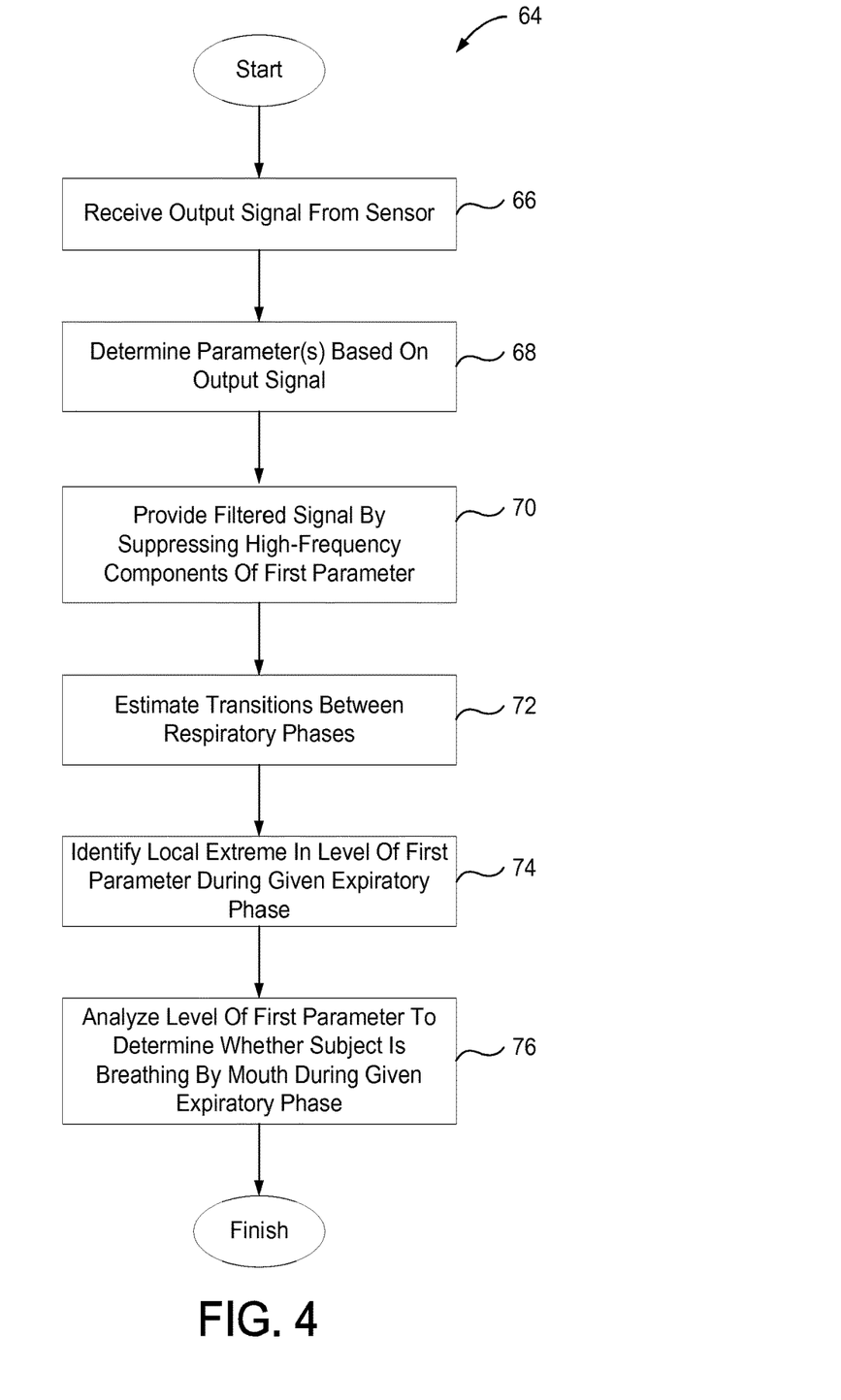
FIG. 4 is a flow chart illustrating a method for detecting mouth-breathing in early phase expiration during respiratory treatments involving a pressure support device, in accordance with one or more embodiments.

FIG. 4 is a flow chart illustrating a method 64 for detecting mouth-breathing in early phase expiration during respiratory treatments involving a pressure support device, in accordance with one or more embodiments. The operations of method 64 presented below are intended to be illustrative. In some implementations, method 64 may be accomplished with one or more additional operations not described, and/or without one or more of the operations discussed. Additionally, the order in which the operations of method 64 are illustrated in FIG. 4 and described below is not intended to be limiting.

In some implementations, method 64 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 64 in response to instructions stored electronically on an electronic storage medium. The one or more processing devices may include one or more devices configured through hardware, firmware, and/or software to be specifically designed for execution of one or more of the operations of method 64.

At an operation 66, an output signal is received from a sensor (e.g., sensor 20). The output signal conveys information relating to one or more parameters of the pressurized flow of breathable gas as it is delivered to an airway of a subject (e.g., subject 12). According to some embodiments, operation 66 is performed by a processor that is the same as or similar to processor 24.

At an operation 68, one or more parameters are determined of the pressurized flow of breathable gas as it is delivered to the airway of the subject based on the output signal. The one or more parameters comprise a first parameter. According to some embodiments, operation 68 is performed by a parameter module that is the same as or similar to parameter module 31.

At an operation 70, a filtered signal is provided by suppressing high-frequency components of the first parameter as a function of time. According to some embodiments, operation 70 is performed by a filter module that is the same as or similar to filter module 32.

At an operation 72, transitions are estimated between inspiratory phases and expiratory phases of respiration by the subject based on the one or more determined parameters. According to some embodiments, operation 72 is performed by a breath delineation module that is the same as or similar to breath delineation module 34.

At an operation 74, a local extreme is identified in a level of the first parameter during a given expiratory phase of respiration by the subject. According to some embodiments, operation 74 is performed by parameter extrema module that is the same as or similar to parameter extrema module 36.

At an operation 76, the level of the first parameter is analyzed as a function of time within a sampling window to determine whether the subject is breathing by mouth during the given expiratory phase. The sampling window begins at or proximate to the identified local extreme in the level of the first parameter. According to some embodiments, operation 76 is performed by a mouth-breathing detection module that is the same as or similar to mouth-breathing detection module 38.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination Although the technology has been described in detail for the purpose of illustration based on what is currently considered to be the most practical and preferred embodiments, it is to be understood that such detail is solely for that purpose and that the technology is not limited to the disclosed embodiments, but, on the contrary, is intended to cover modifications and equivalent arrangements that are within the spirit and scope of the appended claims. For example, it is to be understood that the present technology contemplates that, to the extent possible, one or more features of any embodiment can be combined with one or more features of any other embodiment.

The invention claimed is:

1. A system configured for detecting mouth-breathing in early phase expiration during respiratory treatments involving a pressure support device, the system comprising:
a pressure generator configured to generate a pressurized flow of breathable gas for delivery to the airway of a subject;
a sensor configured to provide an output signal conveying information relating to one or more parameters of the pressurized flow of breathable gas as it is delivered to the airway of the subject; and
one or more processors configured to execute computer program modules, the computer program modules comprising:
a parameter module configured to determine one or more parameters of the pressurized flow of breathable gas as it is delivered to the airway of the subject based on the output signal, the one or more parameters comprising a first parameter;
a filter module configured to smooth bumps, deviations, and/or anomalies in the output signal to provide a filtered signal by suppressing frequencies of high-frequency components and passing frequencies of low-frequency components of the first parameter as a function of time;
a breath delineation module configured to estimate transitions between inspiratory phases and expiratory phases of respiration by the subject based on the one or more parameters determined by the parameter module;
a parameter extrema module configured to identify a local extreme in a level of the first parameter during a given expiratory phase of respiration by the subject; and
a mouth-breathing detection module configured to determine whether the subject is breathing by mouth during the given expiratory phase by analyzing the shape of the level of the first parameter as a function of time within a sampling window, the sampling window beginning at or proximate to the identified local extreme in the level of the first parameter, the analyzing comprising determining a gradient of the level of the first parameter over the sampling window, wherein the mouth-breathing detection module is configured to determine that the subject is breathing by mouth responsive to the gradient being less than or equal to zero following a local minimum in the first parameter.

2. The system of claim 1, wherein the first parameter comprises a flow of breathable gas passing through an interface appliance to the subject, and wherein the breath delineation module is further configured such that estimating the transitions between the inspiratory phases and the expiratory phases includes identifying points where the filtered signal intersects the first parameter as a function of time when the filtered signal and the first parameter as a function of time are plotted together.

3. The system of claim 1, wherein the first parameter comprises a flow of breathable gas passing through an interface appliance to the subject, and wherein the mouth-breathing detection module is further configured such that analyzing the first parameter as a function of time within the sampling window includes determining whether the first parameter within the sampling window increases initially and then becomes flat or decreasing, and wherein a positive determination indicates an occurrence of mouth-breathing by the subject.

4. The system of claim 1, wherein the local extreme in the level of the first parameter is the local minimum.

5. The system of claim 1, wherein the filter module is configured such that the frequencies of the high frequency components are higher than approximately 0.2 Hz, and the frequencies of the low frequency components are lower than approximately 0.1 Hz.

6. The system of claim 1, wherein the mouth-breathing detection module is further configured to down sample the filtered signal, and determine whether the subject is breathing by mouth during the given expiratory phase by analyzing the shape of the level of the first parameter as a function of time within a sampling window based on the down sampled filtered signal.

7. A system configured for detecting mouth-breathing in early phase expiration during respiratory treatments involving a pressure support device, the system comprising:
pressure generation means configured to generate a pressurized flow of breathable gas for delivery to the airway of a subject;
sensor means configured to provide an output signal conveying information relating to one or more parameters of the pressurized flow of breathable gas as it is delivered to the airway of the subject;
parameter determination means configured to determine one or more parameters of the pressurized flow of breathable gas as it is delivered to the airway of the subject based on the output signal, the one or more parameters comprising a first parameter;
filter means configured to smooth bumps, deviations, and/or anomalies in the output signal to provide a filtered signal by suppressing frequencies of high-frequency components and passing frequencies of low-frequency components of the first parameter as a function of time;
breath delineation means configured to estimate transitions between inspiratory phases and expiratory phases of respiration by the subject based on the one or more determined parameters;
minimum flow identification means configured to identify a local extreme in a level of the first parameter during a given expiratory phase of respiration by the subject; and
mouth-breathing detection means configured to determine whether the subject is breathing by mouth during the given expiratory phase by analyzing the shape of the level of the first parameter as a function of time within a sampling window, the sampling window beginning at or proximate to the identified local extreme in the level of the first parameter, the analyzing comprising determining a gradient of the level of the first parameter over the sampling window, wherein the mouth-breathing detection means are configured to determine that the subject is breathing by mouth responsive to the gradient being less than or equal to zero following a local minimum in the first parameter.

8. The system of claim 7, wherein the first parameter comprises a flow of breathable gas passing through an interface appliance to the subject, and wherein the breath delineation means is further configured such that estimating the transitions between the inspiratory phases and the expiratory phases includes identifying points where the filtered signal intersects the first parameter as a function of time when the filtered signal and the first parameter as a function of time are plotted together.

9. The system of claim 7, wherein the first parameter comprises a flow of breathable gas passing through an interface appliance to the subject, and wherein the mouth-breathing detection means is further configured such that analyzing the first parameter as a function of time within the sampling window includes determining whether the first parameter within the sampling window increases initially and then becomes flat or decreasing, and wherein a positive determination indicates an occurrence of mouth-breathing by the subject.

10. The system of claim 7, wherein the local extreme in the level of the first parameter is the local minimum.

11. The system of claim 1, wherein the filter module is configured such that the frequencies of the high frequency components and the frequencies of the low frequency components are numerically different.

12. The system of claim 7, wherein the filter means are configured such that the frequencies of the high frequency components and the frequencies of the low frequency components are numerically different.

13. The system of claim 7, wherein the filter means are configured such that the frequencies of the high frequency components are higher than approximately 0.2 Hz, and the frequencies of the low frequency components are lower than approximately 0.1 Hz.

14. The system of claim 7, wherein the mouth-breathing detection means are further configured to down sample the filtered signal, and determine whether the subject is breathing by mouth during the given expiratory phase by analyzing the shape of the level of the first parameter as a function of time within a sampling window based on the down sampled filtered signal.

* * * * *